United States Patent
Chapman

(10) Patent No.: US 8,227,766 B2
(45) Date of Patent: Jul. 24, 2012

(54) HAND-HELD PROBE FOR INTRA-OPERATIVE DETECTION OF FLUORESCENCE LABELED COMPOUNDS AND ANTIBODIES

(75) Inventor: Gregg J. Chapman, Plain City, OH (US)

(73) Assignee: Navidea Biopharmaceuticals, Inc., Dublin, OH (US)

( * ) Notice: Subject to any disclaimer, the term of this patent is extended or adjusted under 35 U.S.C. 154(b) by 424 days.

(21) Appl. No.: 12/464,855

(22) Filed: May 12, 2009

(65) Prior Publication Data

US 2009/0283698 A1   Nov. 19, 2009

Related U.S. Application Data

(60) Provisional application No. 61/053,470, filed on May 15, 2008.

(51) Int. Cl.
*G01N 21/64* (2006.01)
(52) U.S. Cl. .................................................. 250/458.1
(58) Field of Classification Search ............... 250/458.1, 250/459.1
See application file for complete search history.

(56) References Cited

U.S. PATENT DOCUMENTS

| | | | |
|---|---|---|---|
| 5,130,545 A * | 7/1992 | Lussier | 250/458.1 |
| 6,687,395 B1 | 2/2004 | Dietz et al. | |
| 2001/0046712 A1 | 11/2001 | Hang et al. | |
| 2002/0147317 A1 | 10/2002 | Bentsen et al. | |
| 2003/0160182 A1 * | 8/2003 | Petrich et al. | 250/458.1 |
| 2003/0197855 A1 | 10/2003 | Jung et al. | |
| 2003/0208113 A1 * | 11/2003 | Mault et al. | 600/316 |
| 2004/0235446 A1 * | 11/2004 | Flaherty et al. | 455/352 |
| 2007/0205288 A1 | 9/2007 | Laser | |
| 2008/0011855 A1 | 1/2008 | Nadabar | |

* cited by examiner

*Primary Examiner* — Kiho Kim
(74) *Attorney, Agent, or Firm* — James R. Eley; Michael A. Forhan; Eley Law Firm Co, LPA

(57) ABSTRACT

A hand-held probe for intra-operative detection of fluorescence labeled compounds includes a housing comprising a handle and a columnar portion, and a power source within the housing. A light emission source proximate the columnar portion of the housing is configured to fluoresce at least one of predetermined compounds and predetermined antibodies. An excitation switch proximate the handle selectably activates the light emission source. A detector receives fluorescent light emissions directed toward the columnar portion from at least one of the compounds and antibodies and convert the fluorescent light emissions to a corresponding emission electrical signal. A controller within the housing receives the emission electrical signal from the detector and converts the emission electrical signal to a corresponding data signal. Finally, a data port within the housing receives the data signal from the controller, converts the data signal to a corresponding output signal, and transmits the output signal.

9 Claims, 3 Drawing Sheets

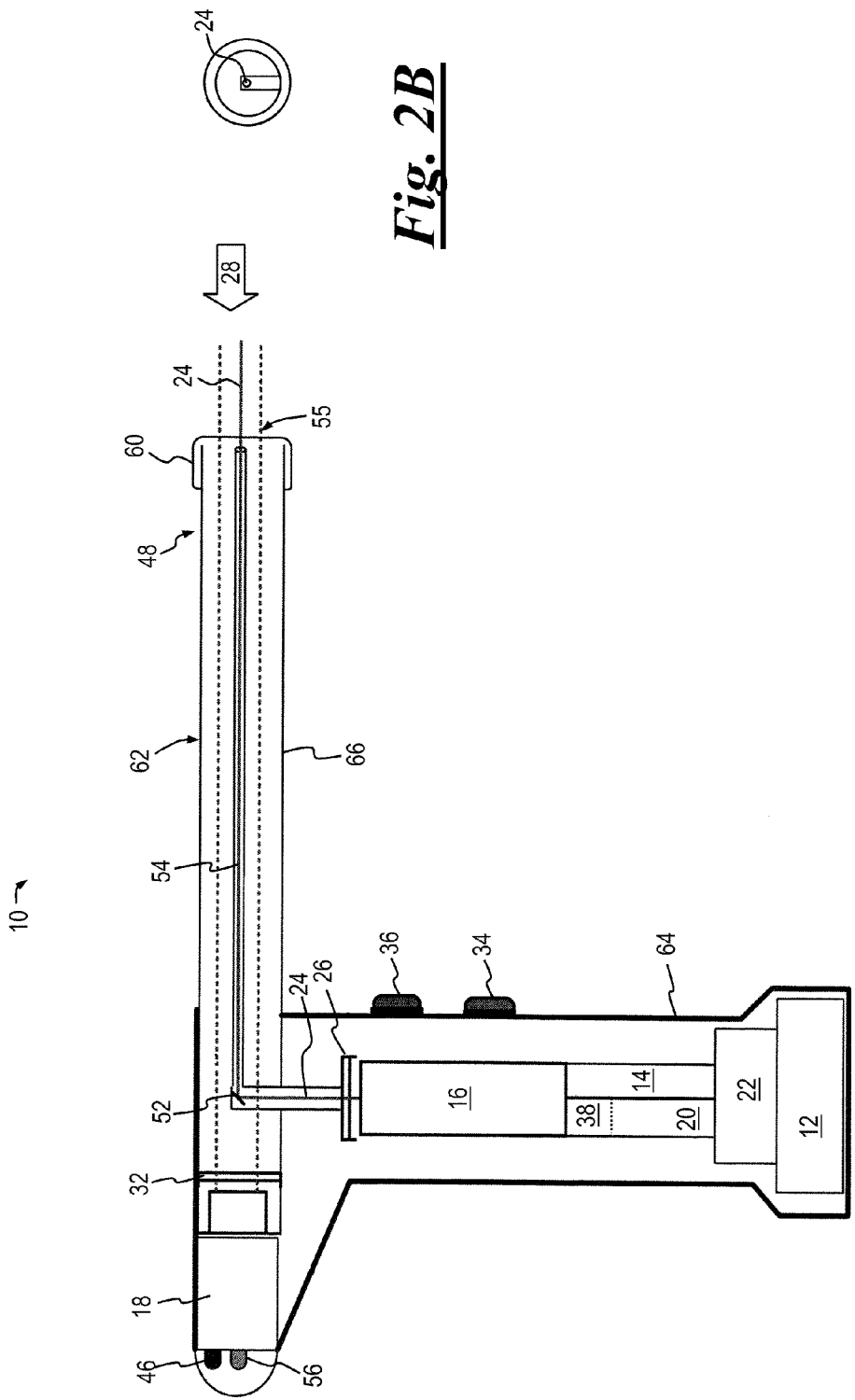

HAND-HELD PROBE FOR INTRA-OPERATIVE DETECTION OF FLUORESCENCE LABELED COMPOUNDS AND ANTIBODIES

This application claims priority to U.S. provisional patent application 61/053,470, filed May 15, 2008, the entire contents of which are hereby incorporated by reference thereto.

FIELD

The present invention relates generally to the identification of particular pathologic tissue and physiologic structures, in particular to intra-operative detection of said tissues and structures by means of fluorescence labeled compounds and antibodies.

BACKGROUND

The recent advent of fluorescence labeling in the field of medicine has led to advanced imaging techniques. These techniques involve the injection of organic fluorophore labeled compounds at the site of target tissue to be examined, such as the site of suspected cancerous animal tissue. Following injection, the fluorophores will tend to accumulate in cancerous tissue in greater concentrations than in non-cancerous tissue. Fluorescence instrumentation is used to detect the accumulated fluorophores and, in turn, identify suspected cancerous tissue.

Fluorescence labeling uses organic fluorophores that are configured to absorb an excitation light at characteristic frequencies for the fluorophore and then emit light having a longer wavelength, also characteristic for the specific fluorophore. Quantum dots, a semiconductor fluorescence marker, have also been used to label organic molecular structures. The quantum dots may be excited at broader wavelengths of light than fluorophores, but like their organic counterparts, emit light having a predetermined characteristic frequency. As fluorescence tagging and imaging becomes more common in the clinical setting, instrumentation to provide excitation and emission detection in a quantitative manner is needed.

Most available fluorescence instrumentation is intended for microscopic applications of ex vivo specimens. To date, in vivo applications have been limited to superimposed images of fluorescence emissions to detect, for example, blood flow and lymphatic structures. Available instruments are relatively large and cumbersome, resulting in limited clinical use. There is a need for a way to more broadly utilize fluorescence labeling in connection with in vivo applications.

SUMMARY

An instrument for intra-operative detection of fluorescence labeled compounds and antibodies is disclosed according to embodiments of the present invention. In some embodiments of the present invention the instrument is portable, hand-held and internally powered. In still other embodiments data generated by the instrument may be transferred to a detection console using a wireless link.

The present invention may be employed for intra-operative detection of fluorescence labeled compounds and antibodies to identify either pathologic tissue or specific physiologic structures, such as lymph nodes. The instrument may be used to detect fluorescent labels on tissue surface, transcutaneously or through soft tissue in an intra-operative setting. Each application preferably utilizes a predetermined excitation light wavelength generated by a light source (such as a laser diode), an excitation filter, an emission filter and a detector. These elements are preferably matched to a select fluorophore or quantum particle to be detected. The present invention may be implemented as either a dedicated probe for a specific fluorophore, using a provided laser diode module and filter set, or implemented as a general purpose instrument, allowing the user to change filters and light modules for a specific fluorophore.

One embodiment of the present invention is a hand-held probe usable for intra-operative detection of fluorescence labeled compounds. The probe includes a housing comprising a handle and a columnar portion, and a power source within the housing. A light emission source proximate the columnar portion is configured to fluoresce at least one of predetermined compounds and predetermined antibodies. An excitation switch proximate the handle selectably activates the light emission source. A detector receives fluorescent light emissions directed toward the columnar portion from at least one of the compounds and antibodies and convert the fluorescent light emissions to a corresponding emission electrical signal. A controller within the housing receives the emission electrical signal from the detector and converts the emission electrical signal to a corresponding data signal. Finally, a data port within the housing receives the data signal from the controller, converts the data signal to a corresponding output signal, and transmits the output signal.

Another embodiment of the present invention is a hand-held fluorescence detection probe comprising a housing having a handle and a columnar portion, and a power source within the housing. A light emission source proximate the columnar portion is configured to fluoresce at least one of predetermined compounds and predetermined antibodies. A mirror is oriented to deflect and direct the emissions from the light emission source out of the probe. A detector receives fluorescent light emissions directed toward the columnar portion from at least one of the compounds and antibodies and converts the fluorescent light emissions to a corresponding emission electrical signal, the detector being positioned behind the mirror. An excitation switch proximate the handle selectably activates the light emission source. A controller within the housing receives the emission electrical signal from the detector and converts the emission electrical signal to a corresponding data signal. Finally, a data port within the housing receives the data signal from the controller, converts the data signal to a corresponding output signal and then transmits the output signal by wireless means.

Yet another embodiment of the present invention is a hand-held fluorescence detection probe, comprising a power source internal to the probe. A light emission source is configured to fluoresce at least one of predetermined compounds and predetermined antibodies. A excitation switch selectably activates the light emission source. A detector receives fluorescent light emissions from at least one of the compounds and antibodies and converts the fluorescent light emissions to a corresponding emission electrical signal, the detector being located behind the light emission source. A fiber-optic ring encircles the light emission source and is laterally separated therefrom, the fiber-optic ring being coupled to the detector. A controller receives the emission electrical signal from the detector and converts the emission electrical signal to a corresponding data signal. Finally, a data port receives the data signal from the controller, converts the data signal to a corresponding output signal and then transmits the output signal by wireless means.

BRIEF DESCRIPTION OF THE DRAWINGS

Further features of the inventive embodiments will become apparent to those skilled in the art to which the embodiments relate from reading the specification and claims with reference to the accompanying drawings, in which:

FIG. 2A is a cutaway view showing the general arrangement of a probe implementation of the instrument of FIG. 1 according to an embodiment of the present invention;

FIG. 2B is a partial end view of the probe of FIG. 2A;

DETAILED DESCRIPTION

Figure 1:
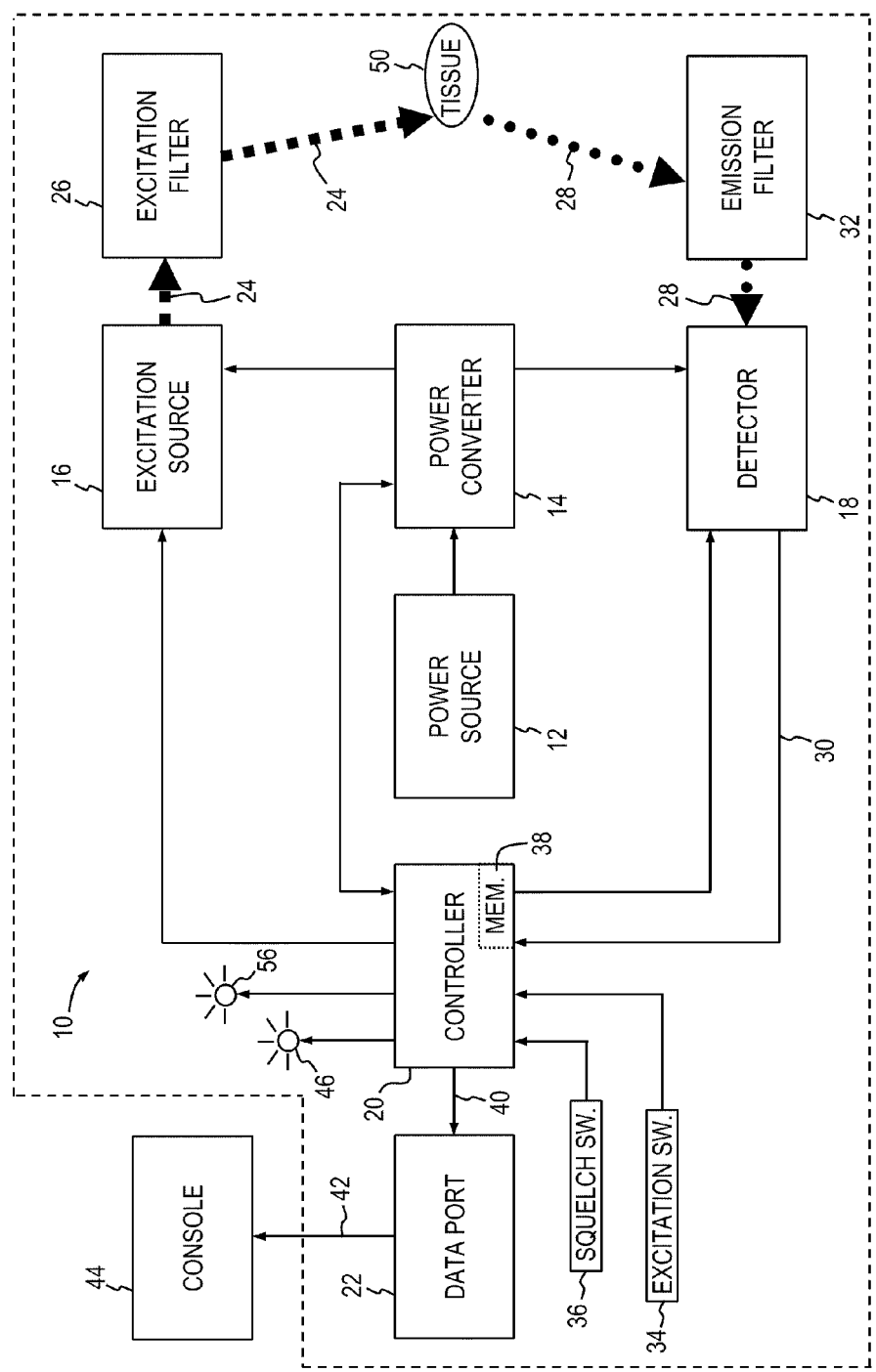
FIG. 1 is a block diagram showing the general arrangement of an instrument usable for the identification of particular pathologic tissue and physiologic structures according to an embodiment of the present invention.

In the discussion that follows, like reference numerals are used to represent like structures and functional elements in the various figures.

A block diagram showing the general arrangement of a hand-held probe 10 for the identification of particular pathologic tissue and physiologic structures is shown in FIG. 1 according to an embodiment of the present invention. Probe 10 comprises in part a power source 12, a power converter 14, an excitation source 16, a detector 18, a controller 20 and a data port 22.

Power source 12 may be any conventional energy supply, such as one or more conventional alkaline, nickel-cadmium or lithium-ion batteries having a predetermined voltage rating. Alternatively, power source 12 may comprise a remote AC or DC power source operated from power mains and coupled to probe 10 with a conventional cable or wire (not shown).

Power converter 14 receives energy from power source 12 and uses that energy to generate one or more power supplies, each having a predetermined voltage level and polarity. For example, power converter 14 may provide +5 volts DC (VDC), −5 VDC and +3.3 VDC output power supplies to various components of probe 10. Power converter 14 may comprise any conventional type of analog and/or switching-type power supply, and may include closed-loop voltage regulation of the output power supplies.

Excitation source 16 comprises a laser diode configured to emit light having a wavelength suitable for exciting a select fluorophore. An excitation light beam 24 emitted by excitation source 16 may optionally be filtered using an excitation filter 26 to reduce the number of wavelengths present in the excitation light beam 24. Accordingly, excitation filter 26 may be configured to limit the passage of light therethrough to certain predetermined wavelengths. In one embodiment, for example, excitation filter 26 may be configured to limit excitation light beam 24 to a narrow bandwidth of about 20 nanometers.

Detector 18 may comprise a photodiode coupled to an amplifier to detect fluorescence light emissions 28. Various types of photodiodes are usable with detector 18 including, without limitation, silicon, PIN and avalanche-type photodiodes. In some embodiments of the present invention the photodiode may further include an integral pre-amplifier. In addition, one or more emission filters 32 may be placed in front of detector 18 to substantially limit the incoming light to the emission wavelength of the fluorophore under study. A resulting emission light magnitude electrical signal 30 is provided to controller 20 by detector 18.

Controller 20 receives control input signals, such as from a laser excitation switch 34 and a squelch switch 36, and controls the operation of at least one of power converter 14, excitation source 16, detector 18 and data port 22. Controller 20 may be any conventional type of microprocessor, microcomputer, computer, or programmable logic device now known or later developed and may include a predetermined set of instructions, such as a computer program, stored in a memory portion 38. The set of instructions allow probe 10 to function in accordance with a predetermined set of criteria, rules and algorithms, as detailed further below. Controller 20 may also include one or more output control signals coupled to any or all of power converter 14, excitation source 16, detector 18 and data port 22. Such control output signals may take any conventional form, such as analog or digital signals, including proprietary and standardized serial and parallel data buses.

Data port 22 receives a data signal 40 from controller 20, the data signal corresponding to emission light magnitude signal 30. Data port 22 converts the data signal 40 to a corresponding output signal 42 having a predetermined data format and then sends the output signal to an external console 44. Data port 22 preferably sends output signal 42 to console 44 in any conventional wireless manner including, without limitation, via modulated infrared and radio frequency signals. In one embodiment the output signal 42 may be configured as BLUETOOTH® (a registered certification mark of Bluetooth Sig., Inc.) protocol using a conventional data protocol, such as a serial port protocol. Alternatively, the output signal 42 may be sent to console 44 by data port 22 through one or more conventional cables or wires connected therebetween. In some embodiments output signal 42 is present only when excitation switch 34 is actuated.

Console 44 receives output signal 42 from data port 22 and displays a visually perceivable, numeric indication corresponding to the magnitude of emission light 28 measured by detector 18. In one embodiment the magnitude of emission light 28 may be represented numerically in units of microwatts. Aural feedback of the relative emission level may also be provided by console 44, the volume and/or frequency of a tone corresponding to the magnitude of emission light 28.

An example probe 10 is shown in FIGS. 2A and 2B. With reference to FIGS. 1, 2A and 2B in combination, probe 10 is operated by first momentarily actuating excitation switch 34. The first actuation of switch 34 preferably does not activate excitation source 16, but instead causes controller 20 to activate the components of probe 10, such as power converter 14 and data port 22, thereby establishing communication between the data port and console 44. A multi-color status indicator 46, such as a light emitting diode (LED) is steadily illuminated to indicate the initial powered-on state of probe 10. Once data port 22 is linked to console 44, status indicator 46 may flash periodically to provide a visual indication of the link. Subsequent actuations of excitation switch 34 will cause excitation source 16 to become active and emit excitation light signal 24.

To use probe 10, an operator places a distal end 48 of the probe proximate target tissue 50 to be tested and actuates excitation switch 34. Excitation light beam 24 emitted by excitation source 16 is filtered through excitation filter 26, then steered within probe 10 using a diagonal mirror 52 and a collimator 54, the excitation light beam being directed out of distal end 48. Excitation light beam 24 is directed toward target tissue 50 to be tested. Tissue 50 containing fluorescent labels will respond to excitation light beam 24 by emitting a fluorescent emission light 28. Emission light 28 enters distal end 48 through a detector aperture 55, where it is filtered by emission filter 32 before being received by detector 18. Detector 18 generates an electrical magnitude signal 30 corresponding to the amount of emission light 28 received by detector 18 and sends the magnitude signal to controller 20. Controller 20 in turn generates a data signal 40 corresponding to magnitude signal 30 and sends the data signal to data port 22. Data port 22 transmits an output signal 42 corresponding to data signal 40 to console 44, which receives the output signal and generates visual and/or aural indications proportional to the magnitude of emission light 28.

Fluorescence emission light 28 measurements by detector 18 may be made more accurate by employing several methods. Firstly, emission filter 32 acts to filter out ambient light and much of the excitation light 24 generated by excitation source 16, thereby preventing much of the excitation light from reaching the detector. Accordingly, one or more emission filters 32 limit the bandwidth of detector 18, although some laser scatter and ambient light will typically exist in the detection band. In addition, one or more excitation filters 26 may be employed to limit excitation light 24 to a relatively narrow bandwidth, typically about 20 nanometers. While filters 24, 32 will not completely eliminate the amount of excitation light presented to detector 18, much of the excitation light is attenuated thereby. It should be noted that in some embodiments of the present invention the wavelengths of excitation light 24 and emission light 28 may overlap slightly.

Another method to improve the measurement accuracy of emission light 28 is to set a squelch threshold for emission light 28 that takes into account ambient lighting conditions. For example, with reference to FIGS. 1, 2A and 2B, probe 10 may be calibrated for a given ambient light level surrounding the target. When probe 10 is first powered (i.e., after excitation switch 34 is initially and momentarily actuated as previously described), the threshold for light detection may be zeroed.

To accomplish this squelch switch 36 may be actuated causing controller 20 to read from detector 18 a value of magnitude signal 30 corresponding to the ambient light level. Controller 20 stores this value which now represents a zero threshold. Preferably, squelch switch 36 is actuated with distal end 48 of probe 10 placed proximate target tissue 50 that is known to lack a significant amount of the fluorophore. The aforementioned zeroing operation is also preferably accomplished with excitation source 16 active (i.e., switch 34 depressed) in order to minimize the contribution of laser scatter from the excitation source to the background light level. After the zero value is established a threshold indicator 56, such as an LED, will illuminate only when the threshold is exceeded.

Alternatively, controller 20 may be configured to illuminate indicator 56 only if the light level exceeds the threshold by a predetermined statistically significant amount. Furthermore, values of data signal 40 exceeding the stored threshold value will be sent to console 44 by data port 22 in the manner previously described. In some embodiments the threshold value may be set to zero by actuating squelch switch 36 for a minimum period of time, signaling controller 20 to set the stored threshold value to zero.

Still another method to improve the measurement accuracy of emission light 28 is to spatially separate excitation light beam 24 and detector 18 such that much of the excitation light beam is not presented to emission filter 32 and/or the detector. Fluorescence detection systems may use an excitation source and detector that are separated using a dichroic mirror or collimation techniques as discussed above and shown in FIGS. 2A and 2B. This technique works well for surface or thin tissue applications. For thicker tissue applications transverse laser excitation may be employed. The target tissue is illuminated from one side and the detector is placed on the other side of the tissue to detect the emission. However, the transverse method is generally impractical for intra-operative applications. Both the transverse and co-axial methods result in laser scatter within the tissue. This often confounds emission measurements, particularly when the fluorophore is deep in the tissue.

Figures 3A, 3B:
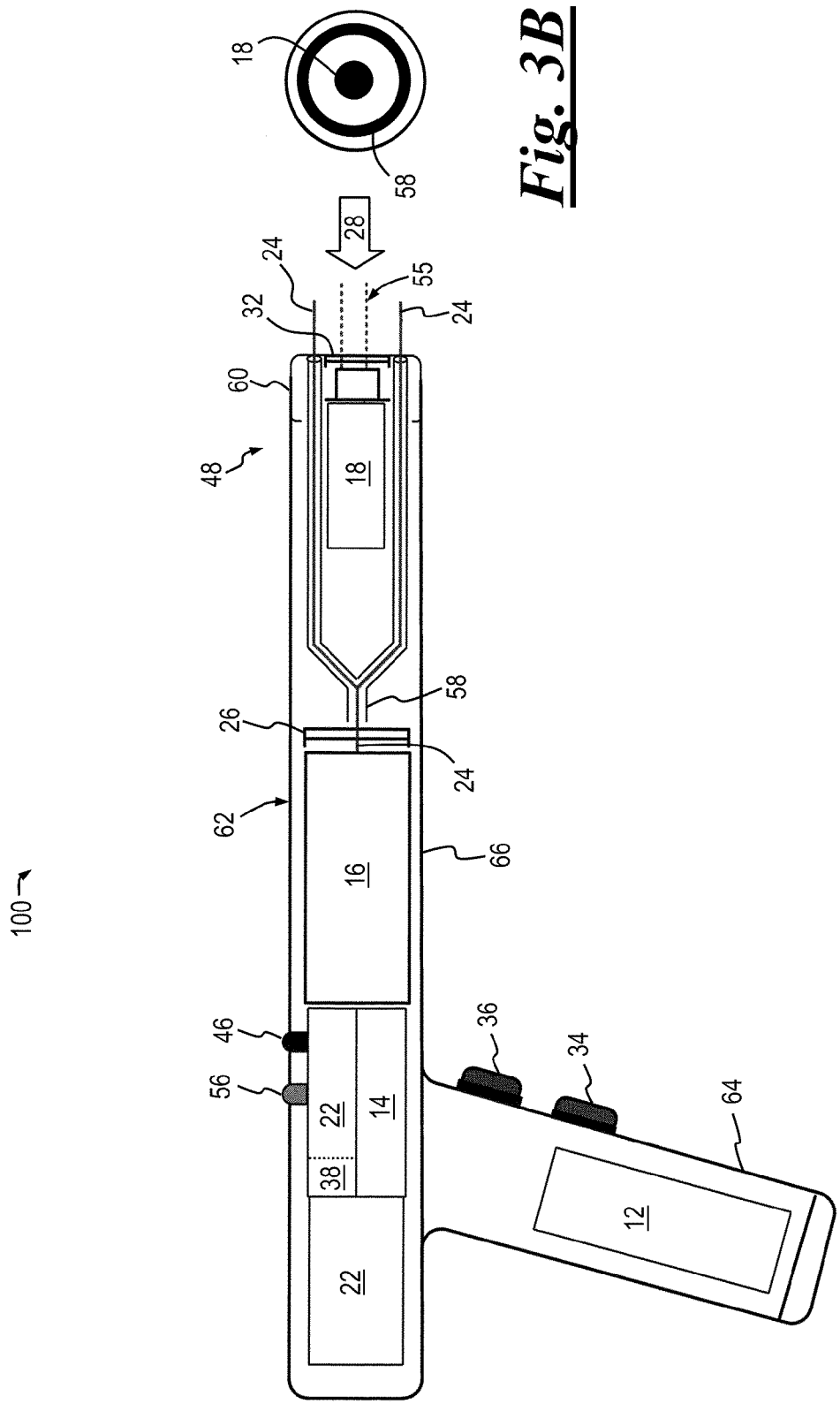
FIG. 3A is a cutaway view showing the general arrangement of a probe implementation of the instrument of FIG. 1 according to another embodiment of the present invention.
FIG. 3B is a partial end view of the probe of FIG. 3A.

To mitigate the contribution of laser scatter, a probe 100, shown in FIGS. 3A and 3B, may be utilized according to another embodiment of the present invention. Probe 100 is configured such that a detector 18 is centered proximate a distal end 48 of the probe and proximate a detector aperture 55. Excitation light 24 from excitation source 16 is presented in a fiber-optic excitation ring 58 that is spatially separated from detector 18. The emission signal 28 from the fluorophore of target tissue 50 is greatest when excitation ring 58 is generally centered over the fluorescent source. By laterally separating excitation ring 58 from emission detector 18, the contribution of laser scattering in tissue 50 to the detected light level is greatly reduced.

Finally, controller 20 may utilize an algorithm stored in memory portion 38 to subtract the contribution of the ambient and excitation light 24 from the fluorescence emission light 28. Subtracting the background level of ambient light by thresholding greatly improves the accuracy of the measured fluorescence emission. Because the background level must be squelched at a different location than the fluorescent target, the proper background level may differ slightly over the targeted tissue. An additional algorithm may be implemented in controller 20 to detect the difference between the tissue emission light 28 with the excitation source 16 "off." Then, a second measurement is made with excitation source 16 "on" (i.e., excitation switch 34 actuated). The difference between the two measurements may be reported to console 44 via output signal 42 in the manner previously discussed. This cycle is repeated for as long as switch 34 is actuated. In another embodiment of the invention measurements may be taken at two different levels of output power of excitation source 16.

Other features of probes 10, 100 include a configuration wherein status indicator 46 may be illuminated in different ways to indicate status information. For example, status indicator 46 may be illuminated in a warning color such as red if the energy level of power source 12 becomes too low for operation of probe 10, 100. In addition, status indicator 46 may flash a predetermined color to indicate that the communication link between data port 22 and console 44 is active and flash yet another predetermined color if the communication link is active and excitation source 16 is also active. Other colors and/or flashing patterns may be used to indicate other states, as desired.

In one embodiment of the present invention laser light beam 24 may be operated in a continuous wave (i.e., uninterrupted-operation) mode. Alternatively, a light rejection algorithm may be used to alternately turn the laser "off" and "on" in a predetermined manner.

Probes 10, 100 may be implemented as a dedicated instrument for a specific predetermined fluorophore, using a predetermined excitation source 16 and filters 26, 32. Alternatively, probes 10, 100 may be provided as a general purpose instrument, allowing the user to change filters 26, 32 and excitation source 16 for use with various fluorophores.

Probes 10, 100 may each optionally include a removable cover 60 to prevent accumulation of foreign materials in distal end 48 and for sanitation purposes.

In some embodiments of the present invention probes 10, 100 may be arranged in a housing 62 comprising a handle 64 and a columnar portion 66 as shown in FIGS. 2A and 3A respectively. This configuration provides a convenient shape for an operator to hold and aim the probe during use.

Some embodiments of the disclosed invention may include one or more of the following aspects. These aspects are presented as examples and are not intended to be limiting. One aspect may be a portable fluorescence excitation/detection device for medical applications, including a device utilizing wireless communications. Another aspect may be a hand-held device for detection of fluorescence in deep tissue. Further aspects may include portable fluorescence detection systems to be used intra-operatively, topically and transcutaneously. The portable fluorescence detection device may be configured to allow interchangeable excitation sources and filtering. Embodiments of the present invention may have an excitation/emission geometry configured to minimize communication between excitation light and emission light detector. Other aspects may include a fluorescence detection device utilizing thresholding and a fluorescence device utilizing difference comparison for excitation off/on or at two power levels. While this invention has been shown and described with respect to a detailed embodiment thereof, it will be understood by those skilled in the art that changes in form and detail thereof may be made without departing from the scope of the claims of the invention.

What is claimed is:

1. A fluorescence detection system, comprising:
   a hand-held probe including:
   a housing comprising a handle and a columnar portion;
   a power source within the housing;
   a light emission source proximate the columnar portion and configured to fluoresce at least one of predetermined compounds and predetermined antibodies;
   an excitation switch proximate the handle to selectably activate the light emission source;
   a detector to receive fluorescent light emissions directed toward the columnar portion from at least one of the compounds and antibodies and convert the fluorescent light emissions to a corresponding emission electrical signal;
   a controller within the housing to receive the emission electrical signal from the detector and convert the emission electrical signal to a corresponding data signal;
   a squelch switch coupled to the controller which, when actuated, causes the controller to read and store in a memory portion a baseline emission electrical signal magnitude for comparison with subsequent emission electrical signals received by the controller from the detector, emission levels having a magnitude below the stored baseline being ignored by the controller; and
   a data port within the housing to receive the data signal from the controller, convert the data signal to a corresponding output signal, and transmit the output signal,
   the system further including a remotely-located console to receive the output signal and provide an indication corresponding to the fluorescent light emissions.

2. The fluorescence detection system of claim 1 wherein the output signal is transmitted by wireless means.

3. The fluorescence detection system of claim 1, further comprising an excitation filter to limit the light emitted by the light emission source to a predetermined bandwidth.

4. The fluorescence detection system of claim 1, further comprising an emission filter to limit the light received by the detector to a predetermined wavelength.

5. The fluorescence detection system of claim 1 wherein the output signal utilizes a predetermined data protocol.

6. The fluorescence detection system of claim 1 wherein the controller is further configured to ignore emission levels exceeding the baseline but having a magnitude less than a predetermined threshold magnitude.

7. The fluorescence detection system of claim 1 wherein the controller is further configured to subtract the contribution of ambient and emission light from the fluorescent light emissions.

8. The fluorescence detection system of claim 1 wherein the indication provided by the console is one of a visually perceivable numeric indication and an aural indication, the indication being proportional to and corresponding with the magnitude of the fluorescent light emissions.

9. The fluorescence detection system of claim 1, further comprising a status indicator mounted to the probe to provide visually perceivable information regarding the status of at least one of the power source, the data port and the remote console.

* * * * *